(12) United States Patent
Dutta et al.

(10) Patent No.: US 8,494,244 B2
(45) Date of Patent: Jul. 23, 2013

(54) SYSTEM AND METHOD FOR BLOOD VESSEL STENOSIS VISUALIZATION AND QUANTIFICATION USING SPECTRAL CT ANALYSIS

(75) Inventors: Sandeep Dutta, Waukesha, WI (US); Darin Robert Okerlund, Muskego, WI (US); Toshihiro Rifu, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 418 days.

(21) Appl. No.: 12/890,835

(22) Filed: Sep. 27, 2010

(65) Prior Publication Data

US 2012/0076377 A1 Mar. 29, 2012

(51) Int. Cl.
*G06K 9/00* (2006.01)

(52) U.S. Cl.
USPC .......................................................... 382/131

(58) Field of Classification Search
None
See application file for complete search history.

(56) References Cited

U.S. PATENT DOCUMENTS

| | | | |
|---|---|---|---|
| 4,541,106 A * | 9/1985 | Belanger et al. | 378/98.11 |
| 7,453,976 B1 * | 11/2008 | Yin | 378/9 |
| 2007/0038061 A1 * | 2/2007 | Huennekens et al. | 600/407 |
| 2007/0041490 A1 * | 2/2007 | Jha et al. | 378/8 |
| 2008/0118021 A1 | 5/2008 | Dutta et al. | |
| 2008/0242977 A1 | 10/2008 | Sirohey et al. | |
| 2009/0161939 A1 * | 6/2009 | Wu et al. | 382/132 |
| 2010/0014737 A1 * | 1/2010 | Ruhrnschopf et al. | 382/131 |
| 2010/0034348 A1 * | 2/2010 | Yu | 378/20 |
| 2010/0195787 A1 | 8/2010 | Flohr et al. | |
| 2010/0202584 A1 * | 8/2010 | Wang et al. | 378/53 |
| 2012/0076377 A1 * | 3/2012 | Dutta et al. | 382/131 |
| 2012/0269317 A1 * | 10/2012 | Fritzler et al. | 378/9 |

FOREIGN PATENT DOCUMENTS

| | | |
|---|---|---|
| DE | 102008010234 A1 | 9/2009 |
| DE | 102008045633 A1 | 3/2010 |

OTHER PUBLICATIONS

Search Report and Written Opinion from EP Application No. 11181423.2 dated Oct. 9, 2012.
Christoph Thomas et al, "Automatic Lumen Segmentation in Calcified Plaques: Dual-Energy CT Versus Standard Reconstructions in Comparison with Digital Subtraction Angiography", American Journal of Roentgenology, vol. 194, No. 6, Jun. 1, 2010, pp. 1590-1595.

(Continued)

*Primary Examiner* — Bhavesh Mehta
*Assistant Examiner* — Tahmina Ansari
(74) *Attorney, Agent, or Firm* — Ziolkowski Patent Solutions Group, SC (57) ABSTRACT

A system and method for dual energy CT spectral imaging that provides for accurate blood vessel stenosis visualization and quantification is disclosed. The CT system includes an x-ray source configured to project x-rays toward a region-of-interest of a patient that includes a blood vessel in a stenosed condition and having a plaque material therein. The CT system also includes an x-ray detector to receive x-rays emitted by the x-ray source and attenuated by the region-of-interest, a data acquisition system (DAS) operably connected to the x-ray detector, and a computer programmed to obtain a first set of CT image data for the region-of-interest at a first chromatic energy level, obtain a second set of CT image data for the region-of-interest at a second chromatic energy level that is higher than the first chromatic energy level, and identify plaque material in the region-of-interest by analyzing the second set of CT image data.

24 Claims, 7 Drawing Sheets

OTHER PUBLICATIONS

Damini Dey et al., "Automated Three-dimensional Quantification of Noncalcified Coronary Plaque from Coronary CT Angiography: Comparison with Intravascular US", Radiology, vol. 257, Sep. 9, 2010, pp. 516-520.

Yu Lifeng et al., "Automatic selection of tube potential for radiation dose reduction in CT: A general strategy", Medical Physics, AIP, Melville, NY, US, vol. 37, No. 1, Dec. 10, 2009, pp. 234-243.

Balazs Ruzsics et al., "Dual-energy CT of the heart for diagnosing coronary artery stenosis and myocardial ischemia—initial experience", European Radiology, Springer, Berlin, DE, vol. 18, No. 11, Jun. 4, 2008, pp. 2414-2424.

Wang Ge et al., "An outlook on x-ray CT research and development", Medical Physics, AIP, Melville, NY, US, vol. 35, No. 3, Feb. 25, 2008, pp. 1051-1064.

* cited by examiner

SYSTEM AND METHOD FOR BLOOD VESSEL STENOSIS VISUALIZATION AND QUANTIFICATION USING SPECTRAL CT ANALYSIS

BACKGROUND OF THE INVENTION

Embodiments of the invention relate generally to diagnostic imaging and, more particularly, to a method and apparatus for dual energy CT spectral imaging that provides for accurate blood vessel stenosis visualization and quantification.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Certain imaging procedures that make use of CT imaging can be challenging based on the presence of imaging artifacts that appear in a reconstructed image (i.e., beam hardening artifacts). For example, accuracy of stenosis measurements in blood vessels is a challenge in CT imaging, especially in the presence of plaque in the vessels that includes high density calcium. The high density calcium plaque in blood vessels introduces a blooming effect that overestimates the true extent of the plaque in the vessel and significantly affects the visualization of the true contrast flow in the vessels. This distorting of the true extent of the plaque in the vessel leads to inaccurate stenosis measurements.

Therefore, it would be desirable to design an apparatus and method that provides for more accurate quantification and visualization of stenosis in blood vessels by reducing the blooming effects of high density plaque in reconstructed CT images.

BRIEF DESCRIPTION OF THE INVENTION

Embodiments of the invention are directed to a method and apparatus for dual energy CT spectral imaging that provides for accurate blood vessel stenosis visualization and quantification. First and second sets of CT image data are acquired at low and high chromatic energy levels, respectively, for a region-of-interest of a patient that includes a blood vessel in a stenosed condition, such that a high-density plaque deposit is present in the blood vessel. The plaque material in the region-of-interest is identified by analyzing the second set of CT image data acquired at the high chromatic energy level, such that the plaque material can be accurately visualized and such that blood vessel stenosis can be accurately quantified.

In accordance with one aspect of the invention, a CT system includes a rotatable gantry having an opening to receive a patient to be scanned and an x-ray source positioned on the rotatable gantry and configured to project x-rays toward a region-of-interest of the patient that includes a blood vessel in a stenosed condition and having a plaque material therein. The CT system also includes an x-ray detector positioned on the rotatable gantry and positioned to receive x-rays emitted by the x-ray source and attenuated by the region-of-interest and a data acquisition system (DAS) operably connected to the x-ray detector. The CT system further includes a computer programmed to obtain a first set of CT image data for the region-of-interest at a first chromatic energy level, obtain a second set of CT image data for the region-of-interest at a second chromatic energy level that is higher than the first chromatic energy level, and identify plaque material in the region-of-interest by analyzing the second set of CT image data.

In accordance with another aspect of the invention, a non-transitory computer readable storage medium has stored thereon a computer program comprising instructions, which, when executed by a computer, cause the computer to cause an x-ray source in a computed tomography (CT) system to emit x-rays at each of a first chromatic energy level and a second chromatic energy level toward a patient during respective first and second scans, with the second chromatic energy level being higher than the first chromatic energy level. The instructions also cause the computer to obtain a first set of CT image data and a second set of CT image data for a region-of-interest of the patient from the respective first and second scans, with the region-of-interest comprising a blood vessel in a stenosed condition that includes a high-density plaque material therein. The instructions further cause the computer to perform an analysis of the second set of CT image data to isolate pixels corresponding to the high-density plaque material in the region-of-interest, reconstruct one of a partial image and a full image of the region-of-interest from the first set of CT image data that includes at least an image of the blood vessel, and apply the isolated pixels corresponding to the high-density plaque material to the one of the partial image and the full image generated from the first set of CT image data to generate a finalized image of the region-of-interest.

In accordance with yet another aspect of the invention, a method of spectral computed tomography (CT) imaging includes the step of acquiring a first set of CT image data for a patient region-of-interest at a low chromatic energy level, with the region-of-interest including a blood vessel structure in a stenosed condition and having a high-density plaque material therein. The method also includes the steps of acquiring a second set of CT image data for the region-of-interest at a high chromatic energy level that is at an increased energy level as compared to the low chromatic energy level and analyzing the first set of CT image data to identify pixels corresponding to the blood vessel structure in the region-of-interest. The method further includes the steps of analyzing the second set of CT image data to identify pixels corresponding to the high-density plaque deposit within the blood vessel structure and reconstructing an image of the region-of-interest from the pixels corresponding to the blood vessel structure identified in the first set of CT image data and the pixels corresponding to the high-density plaque deposit identified in the second set of CT image data.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION

The operating environment of the invention is described with respect to a sixty-four-slice computed tomography (CT) system. However, it will be appreciated by those skilled in the art that the invention is equally applicable for use with single-slice or other multi-slice configurations. Moreover, the invention will be described with respect to the detection and conversion of x-rays. However, one skilled in the art will further appreciate that the invention is equally applicable for the detection and conversion of other high frequency electromagnetic energy. An implementation is employable with a "third generation" CT scanner and/or other CT systems.

Figure 1:
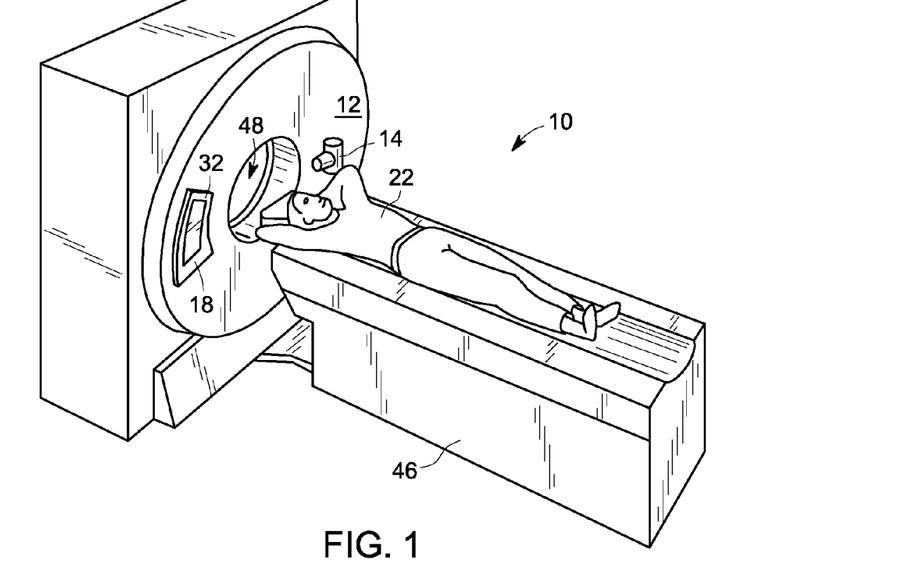
FIG. 1 is a pictorial view of a dual energy CT imaging system for use with embodiments of the invention.
Figure 2:
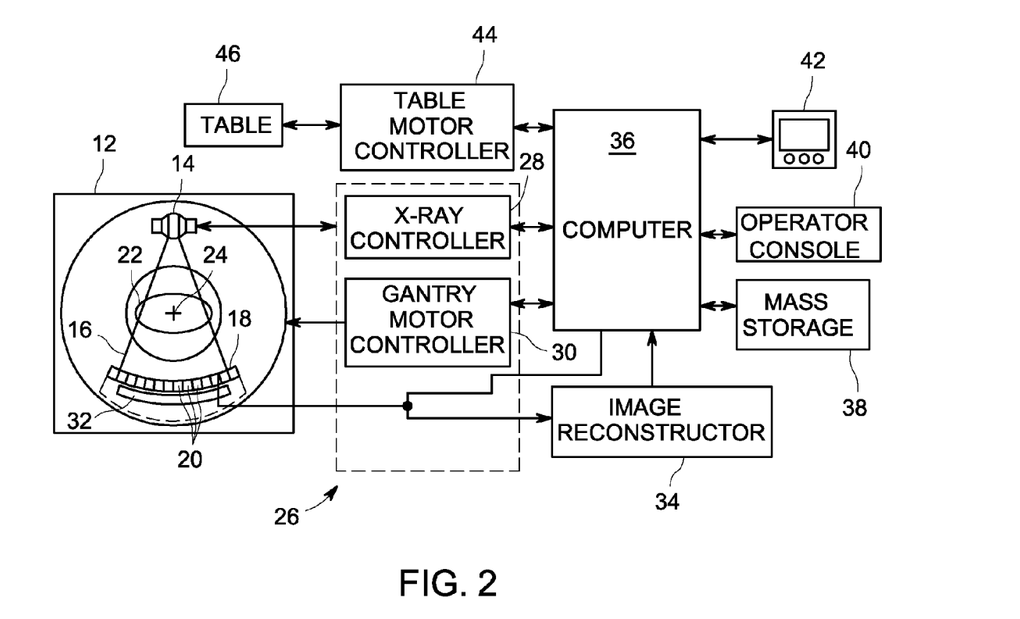
FIG. 2 is a block schematic diagram of the system illustrated in FIG. 1.

Referring to FIG. 1, a computed tomography (CT) imaging system 10 is shown as including a gantry 12 representative of a "third generation" CT scanner. According to an exemplary embodiment of the invention, CT system 10 is provided as a Gemstone Spectral Imaging (GSI) dual energy CT system from GE Healthcare. Gantry 12 has an x-ray source 14 that projects a beam of x-rays 16 toward a detector assembly or collimator 18 on the opposite side of the gantry 12. Referring now to FIG. 2, detector assembly 18 is formed by a plurality of detectors 20 and data acquisition systems (DAS) 32. The plurality of detectors 20 sense the projected x-rays that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24. CT imaging system 10 is a dual-energy system, in that energy is projected from x-ray source 14 at different chromatic energy states in order to enhance contrast separation within image(s).

Rotation of gantry 12 and the operation of x-ray source 14 are governed by a control mechanism 26 of CT system 10. Control mechanism 26 includes an x-ray generator 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray generator 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
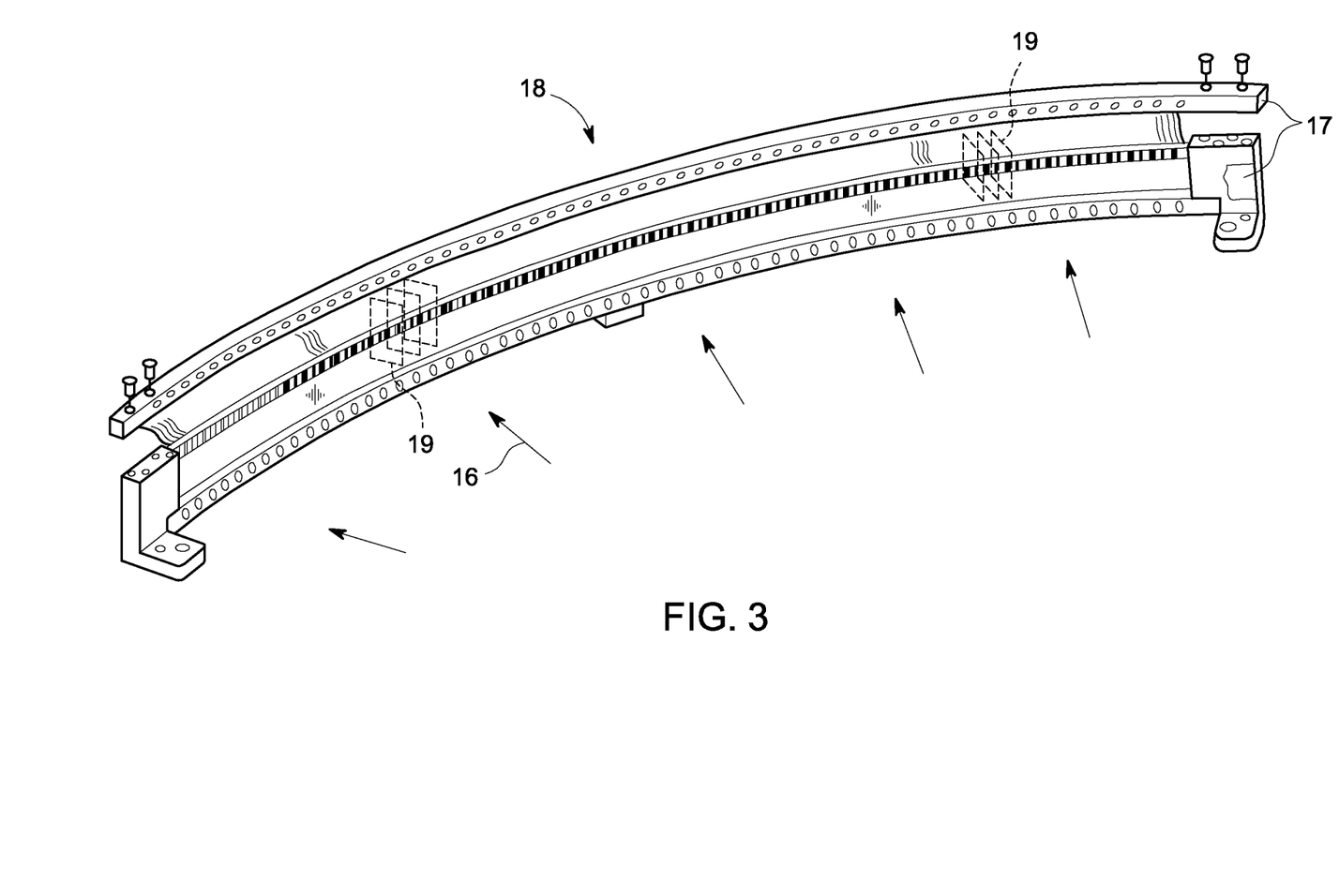
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 channels (16×57 detectors) which allows 64 simultaneous slices of data to be collected with each rotation of gantry 12.

Figure 4:
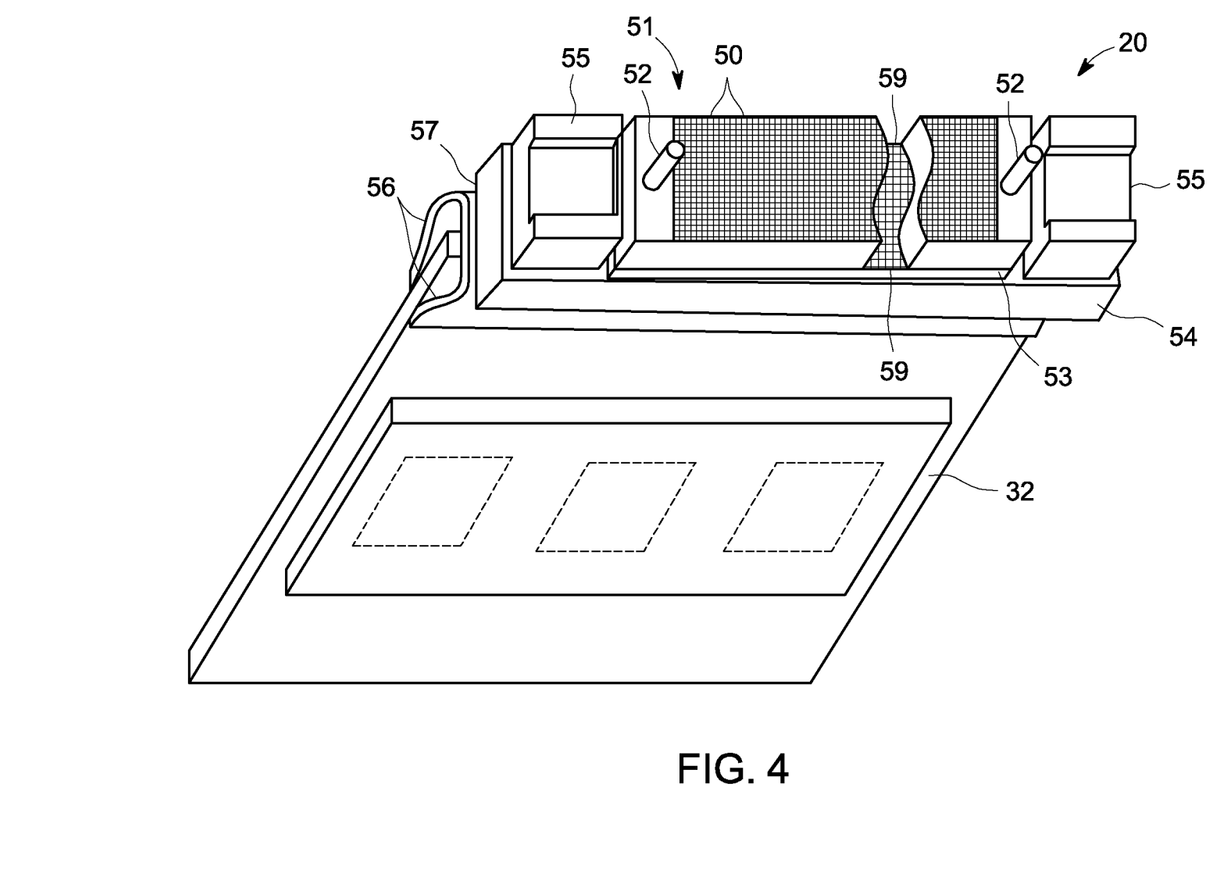
FIG. 4 is a perspective view of one embodiment of a detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

According to embodiments of the invention CT system 10 is operated to obtain CT images of a region-of-interest of a patient that includes a blood vessel structure therein that is partly stenosed (i.e., blocked) form a high density plaque deposit, so as allow for accurate blood vessel stenosis measurements to be made on the blood vessel. When acquiring such images for performing stenosis measurements, it is recognized that the presence of high-density plaque (e.g., calcium plaque) in the vessels that causes the stenosis also hinders the visualization of patency of the vessel in acquired CT images. The beam hardening effects of the plaque create an artificial halo around the vessels in the CT image and lead to a blooming phenomenon that overestimates the amount and volume of plaque in a CT study. This is in addition to the blurring of the actual plaque deposit due to inherent system transfer functions of the CT system.

As set forth above, CT imaging system 10 operates as a dual-energy system, thereby providing for correction for the blooming or beam hardening caused by the high density plaque. CT system 10 utilizes dual-energy scanning to obtain diagnostic CT images that enhance contrast separation within the image by acquiring data of the same locations at two different tube voltage levels (KV). Using the images obtained during the dual energy CT scan, monochromatic images are generated. That is, a monochromatic image can be created at a number of energy levels with each image being at a specific x-ray energy (KeV). While embodiments of the invention described below describe generation of monochromatic images at only two levels, it is recognized that monochromatic images can be created at a greater number of energy levels, such as three, four, or five energy levels, for example. Thus, embodiments of the invention are not limited to the acquiring and generating monochromatic images at only two energy levels (i.e., only a pair of "high" and "low" energy images), and discussion of such here below is not to be construed as such a limitation.

By utilizing dual energy CT, the effect of beam hardening artifact of the high density plaque material can be minimized by looking at the same material at different virtual monochromatic energy levels. That is, high monochromatic energy levels reduce the intensity and corresponding blooming phenomenon of plaque, and that information can be used for the benefit of accurate determination of extent of plaque in the patient vessel. Also the contrast media in the vessels will contribute very little at these high energy and thus the visualization of an exact extent of the high density calcium plaque deposits are possible at these high energy images. By obtaining a CT image at an optimized high monochromatic energy level, the beam hardening artifacts of the high density plaque material will be kept to a determined minimum, thus allowing for accurate visualization of the high density plaque material and accurate quantification of stenosis of the blood vessel.

Figure 5:
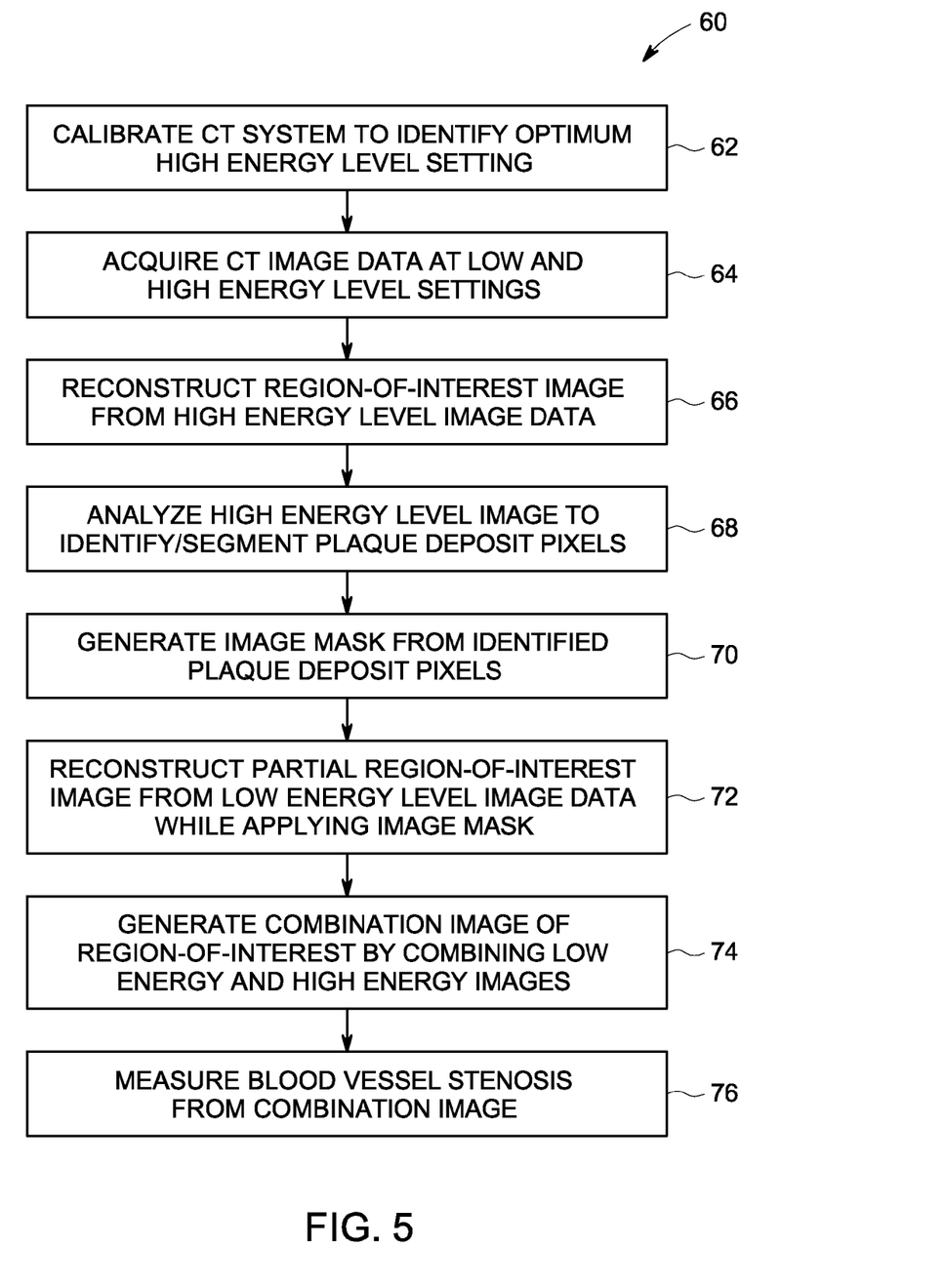
FIG. 5 is a flowchart of a technique for dual energy spectral CT imaging for stenosis visualization and quantification according to an embodiment of the invention.

Referring now to FIG. 5, a technique 60 for reducing the blooming effects of high density plaque in CT images by way of dual energy spectral CT imaging is shown according to an embodiment of the invention, so as to provide for more accurate quantification and visualization of stenosis in vessels. The technique 60 generates a combination vessel patency image for purposes of minimizing beam hardening or blooming associated with high density plaque in the vessel. According to technique 60, a calibration is first performed at STEP 62 to identify an optimum high monochromatic energy level that minimizes the blooming phenomenon/beam hardening in imaging of the plaque deposit. Upon calibration, CT image data is acquired at STEP 64 at a low energy setting and at the determined optimum high energy setting, according to a dual-energy scanning process/image acquisition. Thus, as STEP 64, the low energy image can be acquired at 65 KeV and the high energy image can be acquired at 130 KeV, for example, although it is recognized that other suitable energy levels could also be used, such as another optimum high energy level that is selected based on the calibration results. According to additional embodiments of technique 60, it is also recognized that the high energy image can be acquired at a clinically accepted KeV setting (e.g., 130 KeV) without performing the calibration of STEP 62 or that the calibration of STEP 62 could be done once during the system setup, with the information about behavior of high density calcium samples being stored for use later with CT image data acquired at STEP 64.

With further regard to the acquisition of CT image data at STEP 64, according to an exemplary embodiment of the invention, the CT image data is acquired via scans at two different tube voltage levels (KV), which changes the peak and spectrum of energy of the incident photons comprising the emitted x-ray beams (KeV), via the use of fast switching of the tube voltage. The scans are interleaved as a function of the rotation angle and thus only one gantry rotation around the subject is required to acquire the low energy CT data and the high energy CT data. Thus, beneficially, there is no registration issue with blood vessel and plaque locations on the patient with regard to the low and high energy images, as opposed to if low and high energy CT data were acquired via the use of two tubes (i.e., x-ray sources 14, FIG. 1) or two rotations of the gantry 12 (FIG. 1).

Upon acquisition of CT image data at each of the low and high energy level settings at STEP 64, vessel pixels and plaque region pixels are then selected from CT image data acquired at the most optimal energy level settings with regard to providing contrast in a CT image. According to an exemplary embodiment of the invention, the vessel pixels are selected from the low energy image data (e.g., the 65 KeV image) and the plaque region pixels are selected from the high energy image data, as the blooming effect is minimal in the high energy image data. Thus, in a next step of technique 60, the high energy level image data is processed at STEP 66 to reconstruct a monochromatic image of the region-of-interest. The high energy level image is then analyzed at STEP 68 to identify and segment plaque deposit pixels therefrom. These identified plaque deposit pixels are then used to generate an image mask at STEP 70 that will be applied during generation of the low energy level image. Thus, subsequent to segmentation of the plaque deposit region pixels and generation of the image mask, the low energy level image is processed at STEP 72. In generating the low energy level image, the image mask generated from the plaque deposit pixels is applied such that the masked pixels will be ignored during creation of the low energy level image.

Upon generation of the low energy level image, the plaque pixels from the high energy level image are added onto the low energy level image of the vessel at STEP 74. Thus, a combination image is generated where vessel and other tissues are at a low energy level and the high density plaque is at the high energy level settings. This results in an image where the vessel is at its optimal contrast enhancement but the blooming effect of the plaque deposit is at its minimum. This image can allow the user to see the actual extent of plaque in the vessel. This combination image can be made for any thicknesses, sizes, kernels, entire CT volume or part of it, reformatted slices and even volume rendered and Maximum Intensity Projection images. The plaque pixel images and the rest of the images can also be at different kernel settings. The accurate visualization of the plaque deposit thereby provides for an accurate measurement of the stenosed regions (i.e. of the plaque deposit) at STEP 76, with such a measurement step being performed either automatically by the CT system 10, such as by computer 20, or being performed manually by a system operator.

Figure 6:
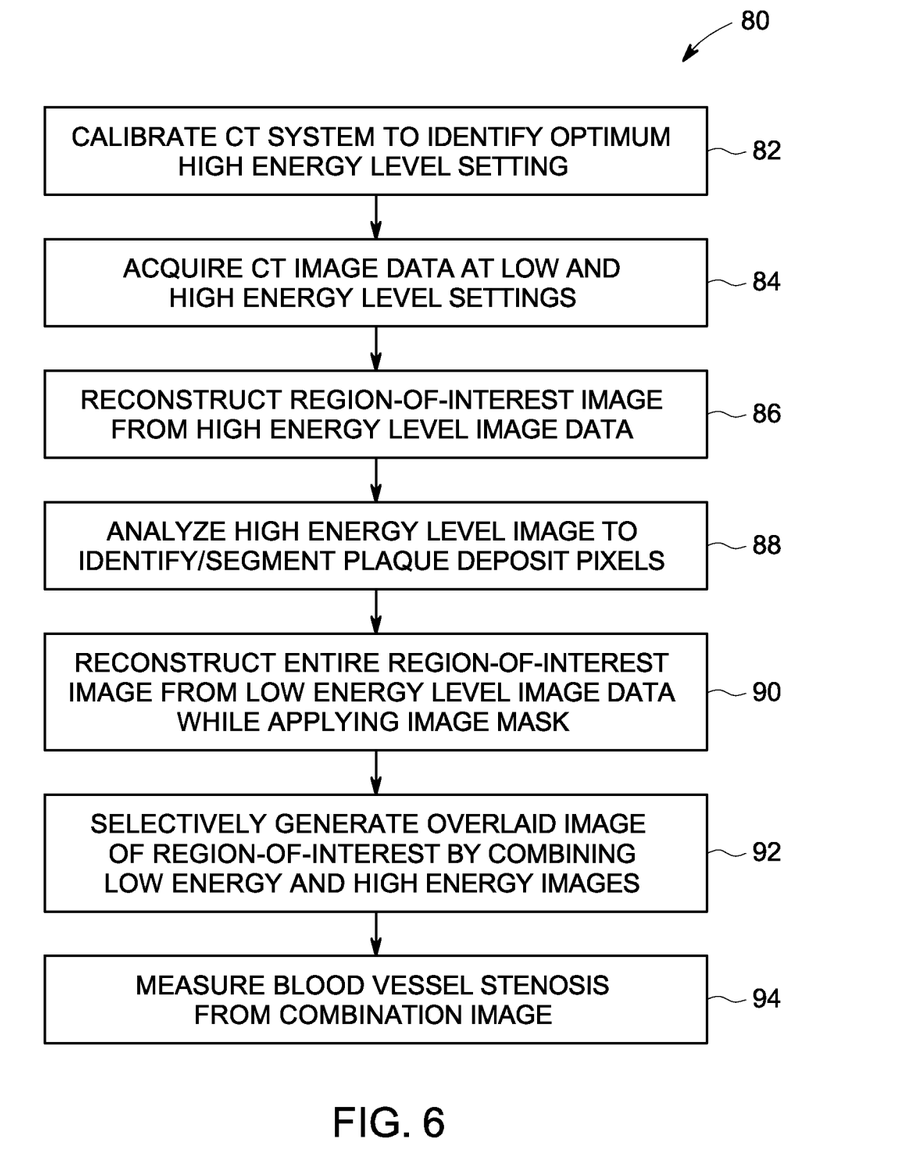
FIG. 6 is a flowchart of a technique for dual energy spectral CT imaging for stenosis visualization and quantification according to another embodiment of the invention.

According to another embodiment of the invention, a technique 80 is provided in FIG. 6 for generating a vessel patency image for purposes of minimizing beam hardening associated with high density plaque. Technique 80 begins at STEP 82, where a calibration is first performed to identify an optimum high monochromatic energy level that minimizes the blooming phenomenon/beam hardening in imaging of the plaque deposit. Alternatively, as set forth above with respect to technique 60 (FIG. 5), it is recognized that the high energy image could be acquired at a clinically accepted KeV setting (e.g., 130 KeV) without performing the calibration. Referring again to technique 80 shown in FIG. 6, upon calibration, CT image data is acquired at STEP 84 at each of a low energy setting and a high energy setting, according to a dual-energy scanning process/image acquisition. For example, the low energy image can be acquired at 65 KeV and the high energy image can be acquired at 130 KeV, although it is recognized that other suitable energy levels could also be used.

Upon acquisition of CT image data at each of the low and high energy levels, the high energy level image data is processed at STEP 86 to reconstruct a monochromatic image of the region-of-interest. The high energy level image is then analyzed at STEP 88 to segment out plaque region pixels from the high energy level image. The plaque region pixels are selected from the high energy image data, as the blooming effect is minimal in the high energy image. The low energy level image data is then processed at STEP 90 to generate an entire CT image at the lower energy setting (e.g., 65 KeV), so as to highlight a better signal to noise ratio of blood vessel/ tissue and contrast media in the CT image. That is, an image including the blood vessel and other tissues, as well as the high density plaque deposit, is generated at STEP 90 from the low energy level image data. This is opposed to technique 60 illustrated in FIG. 5, where selected masked portions were excluded from image reconstruction of the low level energy data, such that only a partial image was reconstructed.

Upon generation of the entire CT image, the plaque region pixel segmented from the high energy level image data is processed and overlaid on the monochromatic low energy level image at STEP 92. According to an exemplary embodiment, the plaque region pixel segmented from the high energy level image data is processed and overlaid on the monochromatic low energy level image is generated in color. The color overlay of the plaque region can be selectively displayed ON and OFF with a keystroke or button choice during visualization. The overlay can become active when the user is ready to take a measurement of the stenosis, for example. At STEP 94, a measurement of the stenosed regions is performed, with such a measurement being made either manually by a user or automatically (e.g., by computer 20 of FIG. 1) based on the extent of the color plaque overlay region.

Figure 7:
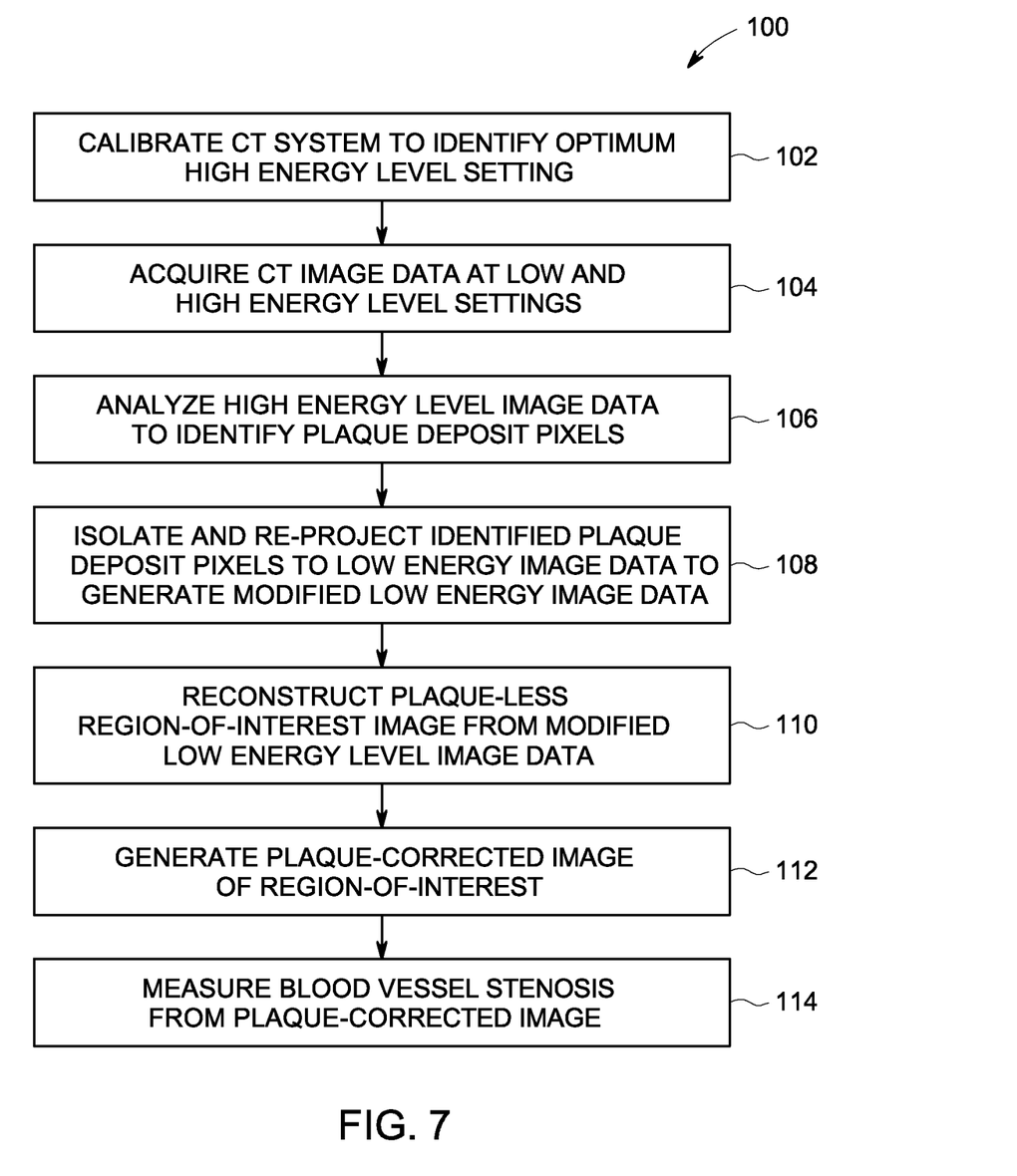
FIG. 7 is a flowchart of a technique for dual energy spectral CT imaging for stenosis visualization and quantification according to another embodiment of the invention.

Referring now to FIG. 7, a technique 100 is set forth for generating a CT image having minimized beam hardening associated with high density plaque in the vessel. According to technique 100, a calibration is first performed at STEP 102 to identify an optimum high monochromatic energy level that minimizes the beam hardening in imaging of the plaque deposit. CT image data is then acquired at STEP 104 at each of a low energy setting and at the optimum high energy setting, according to a dual-energy scanning process/image acquisition. For example, the low energy image can be acquired at 65 KeV and the high energy image can be acquired at 130 KeV, although it is recognized that other suitable energy levels could also be used.

At STEP 106, plaque region pixels are identified from the CT data acquired at an optimal high energy level. Upon such identification of the plaque region pixels in the high energy image, plaque region pixels in the low energy level image data are isolated at STEP 108 and re-projected to the low energy scan data so as to generate a "modified low energy image data" set. A plaque-less image is then generated at STEP 110 by reconstructing the modified low energy level image data, such as via a back projection technique. This reconstruction of the low energy level image data, without inclusion of the plaque region pixels, will reduce the blooming effect or beam hardening in the image, as the image is reconstructed from the raw data without the plaque data. Upon reconstruction of the plaque-less image, the plaque pixels from the high energy level scan are added to the plaque-less image generated from the low energy level image data at STEP 112 as in IBO or beam hardening correction, thus producing a true plaque-corrected image (or a plaque removed image) that provides a more accurate stenosis visualization. A measurement of the blood vessel stenosis is then made at STEP 114 based on the reconstructed image, with such a measurement step being performed either automatically or manually by a system operator.

As set forth above, for each of the techniques 60, 80, 100 of FIGS. 5-7, a measurement can be taken of the blood vessel stenosis based on the reconstructed image illustrating the blood vessel structure and plaque deposit. For the stenosis measurement performed in each of the techniques 60, 80, 100, or for stenosis measurements made on a standardly acquired CT image, corrections to the stenosis measurement can be made to correct for any overestimation of the amount of plaque deposits in the reconstructed image. That is, the stenosis measurements done on a CT image are modified by correcting for the amount of overestimation of plaque deposits usually seen at that image energy level. By utilizing dual energy CT to obtain the Full Width Half Maximum (FWHM) of profiles across plaque deposits for images created at differing monochromatic energy levels, and comparing those FWHM profiles to actual measured sizes of the plaque deposits, a relationship between the monochromatic energy levels and the amount of blooming can be determined. From the use of dual energy CT, it is seen that the FWHM decreases with higher energy levels for all cases. In addition to the effect of the monochromatic energy levels on the FWHM, which is indicative of the blooming effect, the use of clinical visualization settings (window width and level of the images containing these samples) for analyzing the plaque deposit profiles further enhances this relationship between the FWHM and the actual size of the plaque deposit.

In light of the above, it is possible to predict the error in the profile measures of the plaque deposit from actual measures of the plaque deposit at different monochromatic energy levels by taking into consideration the sample density, size, and visualization settings. This information can be easily tabulated experimentally by using a properly designed phantom that can be used as a calibration step of the CT system.

Figure 8:
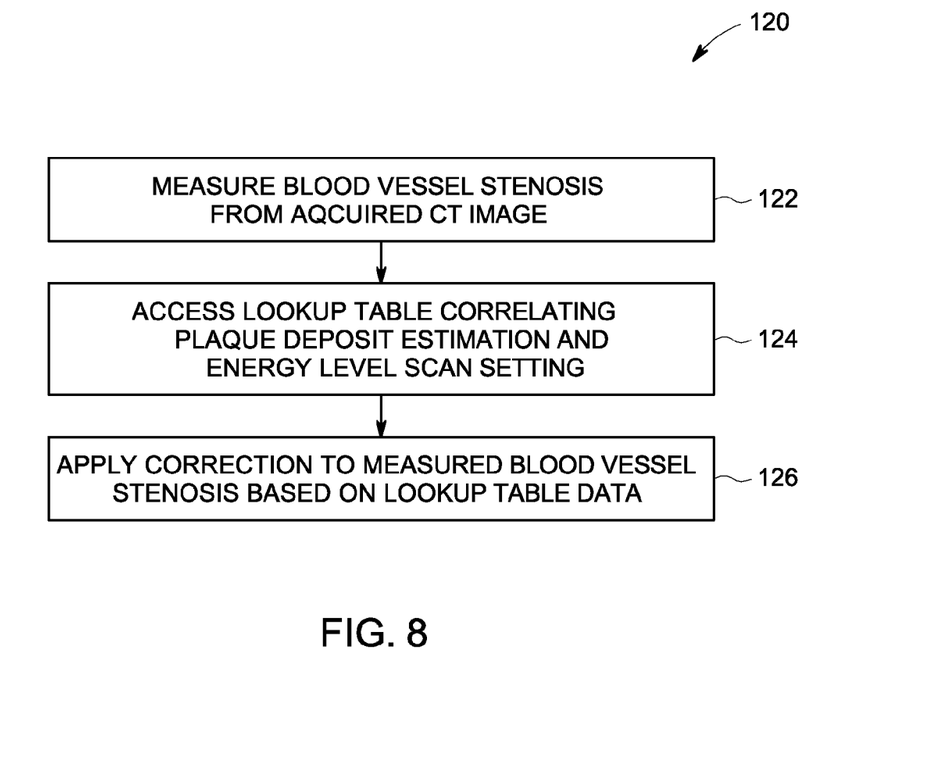
FIG. 8 is a flowchart of a technique for stenosis measurement correction according to an embodiment of the invention.

Referring now to FIG. 8, a technique 120 for correcting stenosis measurements is set forth according to an embodiment of the invention. According to the technique 120, a measurement of the blood vessel stenosis is first made at STEP 122 based on a reconstructed CT image of the blood vessel and the plaque deposit therein, with such a measurement step being performed either automatically or manually by a system operator. Upon measurement of the blood vessel stenosis, a lookup table is accessed at STEP 124 that correlates the amount of overestimation of plaque deposits usually seen at each of a plurality of image energy levels. Such correlations in the lookup table can be based on prior calibration/experimentation comparing FWHM of profiles across plaque deposits for images created at differing monochromatic energy levels to actual measured sizes of plaque deposits, a relationship between the monochromatic energy levels and the amount of blooming can be determined. The lookup table sets forth a suggested correction to the blood vessel stenosis based on the image energy level at which the image data was acquired, and at STEP 126 this correction is applied to generate a corrected blood vessel stenosis measurement.

According to an alternative embodiment of technique 120, it is recognized that a correction to the measured blood vessel stenosis can be determined by way of an equation rather than accessing a lookup table. Such an equation takes into consideration the relationship between measurement error, image window width and window level clinical visualization settings used, density of the plaque material in houndsfield units (HU), and the energy level of the image being measured.

According to another embodiment of the invention, it is recognized that additional steps (e.g., in addition to FWHM-based techniques) can be performed in each of the techniques 60, 80, 100 of FIGS. 5-7 to refine the identified/segmented plaque deposit pixels. For example, a de-convolution process can be performed on the identified/segmented plaque deposit pixels so as to refine the identified plaque material refined for the system transfer function. De-convolution is applied with the point spread function of the reconstruction kernel used. Thus, a de-convolution of the identified calcium regions at high energy after isolating/segmenting such regions corrects or refines the identified calcium, with that corrected information then being added to the low energy images, such that a more accurate sizing of the high density calcium deposits are provided in a finalized image and such that a more accurate stenosis measurement can be performed.

In each of techniques 60, 80, 100 set forth in FIGS. 5-7, it is recognized that still additional refinements and/or alternations to the techniques can be made to improve the stenosis visualization and quantification process. For example, center line information from a low KeV image can be used, along with the reusing of other common points at other energy levels in order to visualize and compare blood vessels in different orientations without having to reprocess the center line of a vessel with contrast at all KeV settings. The optimal contrast level image can be used to get the most accurate center line tracking and the results can be used for all other KeV settings, thus allowing for improved quantification of vessel parameters.

A technical contribution for the disclosed method and apparatus is that is provides for a computer implemented method and apparatus for dual energy CT spectral imaging that provides for accurate blood vessel stenosis visualization and quantification.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not listed may be employed with embodiments of the invention.

A number of such components can be combined or divided in an implementation of a system. Further, such components may include a set and/or series of computer instructions written in or implemented with any of a number of programming languages, as will be appreciated by those skilled in the art.

Therefore, according to one embodiment of the invention, a CT system includes a rotatable gantry having an opening to receive a patient to be scanned and an x-ray source positioned on the rotatable gantry and configured to project x-rays toward a region-of-interest of the patient that includes a blood vessel in a stenosed condition and having a plaque material therein. The CT system also includes an x-ray detector positioned on the rotatable gantry and positioned to receive x-rays emitted by the x-ray source and attenuated by the region-of-interest and a data acquisition system (DAS) operably connected to the x-ray detector. The CT system further includes a computer programmed to obtain a first set of CT image data for the region-of-interest at a first chromatic energy level, obtain a second set of CT image data for the region-of-interest at a second chromatic energy level that is higher than the first chromatic energy level, and identify plaque material in the region-of-interest by analyzing the second set of CT image data.

According to another embodiment of the invention, a non-transitory computer readable storage medium has stored thereon a computer program comprising instructions, which, when executed by a computer, cause the computer to cause an x-ray source in a computed tomography (CT) system to emit x-rays at each of a first chromatic energy level and a second chromatic energy level toward a patient during respective first and second scans, with the second chromatic energy level being higher than the first chromatic energy level. The instructions also cause the computer to obtain a first set of CT image data and a second set of CT image data for a region-of-interest of the patient from the respective first and second scans, with the region-of-interest comprising a blood vessel in a stenosed condition that includes a high-density plaque material therein. The instructions further cause the computer to perform an analysis of the second set of CT image data to isolate pixels corresponding to the high-density plaque material in the region-of-interest, reconstruct one of a partial image and a full image of the region-of-interest from the first set of CT image data that includes at least an image of the blood vessel, and apply the isolated pixels corresponding to the high-density plaque material to the one of the partial image and the full image generated from the first set of CT image data to generate a finalized image of the region-of-interest.

According to yet another embodiment of the invention, a method of spectral computed tomography (CT) imaging includes the step of acquiring a first set of CT image data for a patient region-of-interest at a low chromatic energy level, with the region-of-interest including a blood vessel structure in a stenosed condition and having a high-density plaque material therein. The method also includes the steps of acquiring a second set of CT image data for the region-of-interest at a high chromatic energy level that is at an increased energy level as compared to the low chromatic energy level and analyzing the first set of CT image data to identify pixels corresponding to the blood vessel structure in the region-of-interest. The method further includes the steps of analyzing the second set of CT image data to identify pixels corresponding to the high-density plaque deposit within the blood vessel structure and reconstructing an image of the region-of-interest from the pixels corresponding to the blood vessel structure identified in the first set of CT image data and the pixels corresponding to the high-density plaque deposit identified in the second set of CT image data.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:
1. A CT system comprising:
a rotatable gantry having an opening to receive a patient to be scanned;
an x-ray source positioned on the rotatable gantry and configured to project x-rays toward a region-of-interest of the patient that includes a blood vessel in a stenosed condition and having a plaque material therein;

an x-ray detector positioned on the rotatable gantry and positioned to receive x-rays emitted by the x-ray source and attenuated by the region-of-interest;

a data acquisition system (DAS) operably connected to the x-ray detector; and a computer programmed to:
  obtain a first set of CT image data for the region-of-interest at a first chromatic energy level;
  obtain a second set of CT image data for the region-of-interest at a second chromatic energy level that is higher than the first chromatic energy level;
  identify plaque material in the region-of-interest by analyzing the second set of CT image data;
  isolate the identified plaque material pixels from the second set of CT image data;
  reconstruct one of a partial image and a full image of the region-of-interest from the first set of CT image data that includes at least an image of the blood vessel; and
  apply the isolated pixels corresponding to the plaque material to the one of the partial image and the full image generated from the first set of CT image data to generate a finalized image of the region-of-interest.

2. The CT system of claim 1 wherein the computer is further programmed to:
  perform a calibration of the CT system to determine a chromatic energy level at which beam hardening associated with imaging of the plaque material is minimized; and
  set the second chromatic energy level at an energy level setting that minimizes beam hardening associated with imaging of the plaque material based on the calibration of the CT system.

3. The CT system of claim 1 wherein the computer is further programmed to reconstruct a combination image of the region-of-interest using a portion of each of the first set of CT image data and the second set of CT image data, wherein the blood vessel in the combination image is reconstructed from the first set of CT image data and the plaque material in the combination image is reconstructed from the second set of CT image data.

4. The CT system of claim 3 wherein the computer is further programmed to:
  reconstruct a first monochromatic image of the region-of-interest from the second set of CT image data;
  identify and segment out plaque material pixels from the reconstructed first monochromatic image;
  generate an image mask from the segmented plaque material pixels;
  reconstruct a second monochromatic image of the region-of-interest from the first set of CT image data while applying the image mask, such that pixels masked by the image mask are excluded from the reconstruction of the second monochromatic image; and
  add the segmented plaque material pixels to the second image to form the combination image of the region-of-interest.

5. The CT system of claim 1 wherein the computer is further programmed to generate a multi-layer image of the region-of-interest using the first set of CT image data and the second set of CT image data, wherein a complete image of the region-of-interest is reconstructed from the first set of CT image data and a selectively displayable image of the plaque material is reconstructed from the second set of CT image data.

6. The CT system of claim 5 wherein the computer is further programmed to:
  reconstruct a first monochromatic image of the region-of-interest from the second set of CT image data;
  identify and segment out plaque material pixels from the reconstructed first monochromatic image to generate a plaque material image overlay;
  reconstruct a second monochromatic image of the region-of-interest from the first set of CT image data, the second monochromatic image comprising an entire image of the region-of-interest and including both the blood vessel and the plaque material; and
  selectively display the plaque material image overlay on the second monochromatic image.

7. The CT system of claim 6 wherein the computer is further programmed to display the plaque material image overlay in color on the second monochromatic image.

8. The CT system of claim 1 wherein the computer is further programmed to:
  identify plaque material pixels in the second set of CT image data;
  isolate the identified plaque material pixels from the second set of CT image data;
  re-project the isolated plaque material pixels to the first set of CT image data to generate a modified first set of CT image data;
  reconstruct a plaque-free monochromatic image of the blood vessel from the modified first set of CT image data; and
  add the isolated plaque material pixels to the plaque-free monochromatic image to generate a plaque-corrected image.

9. The CT system of claim 1 wherein the computer is further programmed to:
  reconstruct an image of the region-of-interest using at least a portion of each of the first set of CT image data and the second set of CT image data;
  perform a stenosis measurement on the blood vessel in the reconstructed image based on the amount of plaque material identified by analysis of the second set of CT image data.

10. The CT system of claim 9 wherein the computer is further programmed to:
  access a look-up table providing a correlation between chromatic energy levels employed for a scan and over-estimation error of plaque material size associated with such chromatic energy levels; and
  apply a correction to the stenosis measurement based on the look-up table correlations.

11. The CT system of claim 1 wherein the computer is further programmed to obtain the first and second sets of CT image data during a single rotation of the rotatable gantry and using a single x-ray source.

12. The CT system of claim 1 wherein the computer is further programmed to perform a de-convolution on the identified plaque material in the region-of-interest to refine the identified plaque material.

13. A non-transitory computer readable storage medium having stored thereon a computer program comprising instructions, which, when executed by a computer, cause the computer to:
  cause an x-ray source in a computed tomography (CT) system to emit x-rays at each of a first chromatic energy level and a second chromatic energy level toward a patient during respective first and second scans, the second chromatic energy level being higher than the first chromatic energy level;
  obtain a first set of CT image data and a second set of CT image data for a region-of-interest of the patient from the respective first and second scans, the region-of-interest comprising a blood vessel in a stenosed condition that includes a high-density plaque material therein;

perform an analysis of the second set of CT image data to isolate pixels corresponding to the high-density plaque material in the region-of-interest;

reconstruct one of a partial image and a full image of the region-of-interest from the first set of CT image data that includes at least an image of the blood vessel; and apply the isolated pixels corresponding to the high-density plaque material to the one of the partial image and the full image generated from the first set of CT image data to generate a finalized image of the region-of-interest.

14. The non-transitory computer readable storage medium of claim 13 wherein the instructions further cause the computer to:

reconstruct a monochromatic image of the region-of-interest from the second set of CT image data;

segment out the isolated pixels corresponding to the high-density plaque material from the reconstructed monochromatic image;

generate an image mask from the isolated pixels corresponding to the high-density plaque material;

apply the image mask during reconstruction of the image of the region-of-interest from the first set of CT image data, such that a partial image of the region-of-interest including only the blood vessel is generated; and apply the isolated pixels corresponding to the high-density plaque material to the partial image of the region-of-interest to generate a combination finalized image of the region-of-interest, wherein the combination finalized image includes an image of the blood vessel generated from the first set of CT image data and an image of the high-density plaque material generated from the second set of CT image data.

15. The non-transitory computer readable storage medium of claim 13 wherein the instructions further cause the computer to:

reconstruct a monochromatic image of the region-of-interest from the second set of CT image data;

segment out the isolated pixels corresponding to the high-density plaque material from the reconstructed monochromatic image;

reconstruct a full image of the region-of-interest from the first set of CT image data that includes both the blood vessel and the high-density plaque material; and selectively apply the isolated pixels corresponding to the high-density plaque material to the full image of the region-of-interest to generate the finalized image of the region-of-interest, wherein the selectively applied isolated pixels corresponding to the high-density plaque material are overlaid in color onto the full image of the region-of-interest.

16. The non-transitory computer readable storage medium of claim 13 wherein the instructions further cause the computer to:

re-project the isolated pixels corresponding to the high-density plaque material to the first set of CT image data to generate a modified first set of CT image data;

reconstruct a partial image of the region-of-interest from the modified first set of CT image data, the partial image comprising a plaque-free monochromatic image of the blood vessel; and apply the isolated pixels corresponding to the high-density plaque material to the partial image of the region-of-interest to generate a plaque-corrected finalized image.

17. The non-transitory computer readable storage medium of claim 13 wherein the instructions further cause the computer to:

perform a stenosis measurement on the blood vessel in the finalized image based on the isolated pixels corresponding to the high-density plaque material in the region-of-interest as determined by analysis of the second set of CT image data;

access a look-up table providing a correlation between chromatic energy levels employed for a scan and over-estimation error of plaque material size associated with such chromatic energy levels; and apply a correction to the stenosis measurement based on the look-up table correlations.

18. The non-transitory computer readable storage medium of claim 13 wherein the instructions further cause the computer to perform a de-convolution on the identified plaque material in the region-of-interest to refine the identified plaque material.

19. A method of spectral computed tomography (CT) imaging comprising:

acquiring a first set of CT image data for a patient region-of-interest at a low chromatic energy level, the region-of-interest including a blood vessel structure in a stenosed condition and having a high-density plaque material therein;

acquiring a second set of CT image data for the region-of-interest at a high chromatic energy level, the high chromatic energy level being at an increased energy level as compared to the low chromatic energy level;

analyzing the first set of CT image data to identify pixels corresponding to the blood vessel structure in the region-of-interest;

analyzing the second set of CT image data to identify pixels corresponding to the high-density plaque deposit within the blood vessel structure;

isolating the identified pixels corresponding to the high-density plaque deposit from the second set of CT image data;

reconstructing one of a partial image and a full image of the region-of-interest from the first set of CT image data that includes at least an image of the blood vessel; and applying the isolated pixels corresponding to the high-density plaque deposit to the one of the partial image and the full image generated from the first set of CT image data to generate a finalized image of the region-of-interest.

20. The method of claim 19 further comprising:

determining a chromatic energy level at which beam hardening associated with imaging of the high-density plaque material is minimized; and set the second chromatic energy level at the energy level setting that is determined to minimize beam hardening associated with imaging of the plaque material.

21. The method of claim 19 wherein analyzing the first and second sets of CT image data and reconstructing the image of the region-of-interest comprises:

reconstructing a monochromatic image of the region-of-interest from the second set of CT image data;

isolating the identified pixels corresponding to the high-density plaque material from the reconstructed monochromatic image;

generating an image mask from the isolated pixels corresponding to the high-density plaque material;

applying the image mask during reconstruction of an image of the region-of-interest from the first set of CT image data, such that a partial image of the region-of-interest including only the blood vessel is generated; and applying the isolated pixels corresponding to the high-density plaque material to the partial image of the region-of-interest to generate a combination image of the region-of-interest, wherein the combination image includes an image of the blood vessel generated from the first set of CT image data and an image of the high-density plaque material generated from the second set of CT image data.

22. The method of claim 19 wherein analyzing the first and second sets of CT image data and reconstructing the image of the region-of-interest comprises:

reconstructing a monochromatic image of the region-of-interest from the second set of CT image data;

isolating the identified pixels corresponding to the high-density plaque material from the reconstructed monochromatic image;

reconstructing a full image of the region-of-interest from the first set of CT image data that includes both the blood vessel and the high-density plaque material; and selectively applying the isolated pixels corresponding to the high-density plaque material to the full image of the region-of-interest to generate an overlaid image of the region-of-interest, wherein the selectively applied isolated pixels corresponding to the high-density plaque material are overlaid in color onto the full image of the region-of-interest.

23. The method of claim 19 wherein analyzing the first and second sets of CT image data and reconstructing the image of the region-of-interest comprises:

re-projecting the identified pixels corresponding to the high-density plaque material to the first set of CT image data to generate a modified first set of CT image data;

reconstructing a partial image of the region-of-interest from the modified first set of CT image data, the partial image comprising a plaque-free monochromatic image of the blood vessel; and applying the identified pixels corresponding to the high-density plaque material to the partial image of the region-of-interest to generate a plaque-corrected finalized image.

24. The method of claim 19 wherein acquiring the first and second sets of CT image data comprises obtaining the first and second sets of CT image data during a single rotation of a rotatable gantry of a CT system, with an x-ray source on the rotatable gantry being switching between a low energy level and a high energy level such that the first and second sets of CT image data are acquired in an interleaved scanning pattern.

\* \* \* \* \*